United States Patent
Fotinos et al.

(10) Patent No.: US 7,083,781 B2
(45) Date of Patent: Aug. 1, 2006

(54) FILM FORMING POLYMERS, METHODS OF USE, AND DEVICES AND APPLICATIONS THEREOF

(75) Inventors: Spiros Fotinos, Athens (GR); Ekaterini Tsardaka, Athens (GR); George Koborozos, Athens (GR)

(73) Assignee: Lavipharm S.A., Peania Attica (GR)

( * ) Notice: Subject to any disclaimer, the term of this patent is extended or adjusted under 35 U.S.C. 154(b) by 0 days.

(21) Appl. No.: 10/408,845

(22) Filed: Apr. 7, 2003

(65) Prior Publication Data

US 2003/0224053 A1 Dec. 4, 2003

Related U.S. Application Data

(63) Continuation-in-part of application No. 09/537,318, filed on Mar. 29, 2000, now abandoned.

(60) Provisional application No. 60/149,751, filed on Aug. 19, 1999.

(51) Int. Cl.
- A61K 31/74 (2006.01)
- A61K 9/14 (2006.01)
- A61Q 1/02 (2006.01)

(52) U.S. Cl. .................. 424/78.31; 424/486; 424/401

(58) Field of Classification Search ............. 424/486, 424/401, 59, 78.31, 400, 78.03; 514/263.3, 514/557

See application file for complete search history.

(56) References Cited

U.S. PATENT DOCUMENTS

| | | | |
|---|---|---|---|
| 4,696,821 A | 9/1987 | Belsole | 424/448 |
| 4,812,313 A | 3/1989 | Gale | 424/448 |
| 4,954,344 A | 9/1990 | Gale | 424/448 |
| 5,059,187 A | 10/1991 | Sperry et al. | 604/290 |
| 5,152,997 A | 10/1992 | Ebert et al. | 424/449 |
| 5,234,140 A | 8/1993 | Demarest et al. | 222/394 |
| 5,302,395 A | 4/1994 | Ebert et al. | 424/449 |
| 5,480,648 A | 1/1996 | Wendel et al. | 424/448 |
| 5,482,710 A | 1/1996 | Slavtcheff et al. | 424/195.1 |
| 5,618,515 A | 4/1997 | Singh et al. | 424/45 |
| 5,679,324 A | 10/1997 | Lisboa et al. | 424/45 |
| 5,746,354 A | 5/1998 | Perkins | 222/132 |
| 5,747,022 A * | 5/1998 | Slavtcheff | 424/78.03 |
| 5,769,283 A | 6/1998 | Owada et al. | 222/402.2 |
| 5,925,372 A | 7/1999 | Berner et al. | 424/448 |
| 6,007,836 A | 12/1999 | Denzer | 424/449 |
| 6,008,246 A | 12/1999 | Ito et al. | 514/458 |
| 6,159,485 A | 12/2000 | Yu et al. | 424/401 |

FOREIGN PATENT DOCUMENTS

EP 0987 017 A1 3/2000

(Continued)

OTHER PUBLICATIONS

XP-002151323 and JP 57209215, Mitsubishi Dec. 22, 1982.

(Continued)

*Primary Examiner*—Michael Hartley
*Assistant Examiner*—Blessing Fubara
(74) *Attorney, Agent, or Firm*—Bromberg & Sunstein LLP (57) ABSTRACT

Compositions and methods for delivering active agents to the skin of a subject, including a polymer, an active ingredient and a solvent are disclosed, the compositions being capable of delivery by rolling, spreading, aerosol or in droplets and of forming a film in contact with the skin.

36 Claims, 1 Drawing Sheet

FOREIGN PATENT DOCUMENTS

| | | |
|---|---|---|
| FR | 2710649 A1 | 7/1995 |
| GB | 1108 837 A | 4/1968 |
| JP | 57-209215 | 12/1982 |
| WO | WO 94/23581 | 10/1994 |
| WO | WO 95/03778 | 9/1995 |
| WO | WO 98/58628 | 12/1998 |
| WO | WO 00/16752 | 3/2000 |
| WO | WO 01/13955 | 3/2001 |

OTHER PUBLICATIONS

"Mask a astringents/toners" "Textbook of Cosmetic Dermatology," published Maritin Dunitz, ISBN 1-85317-478-5 and edited by Robert Baran and Howard Maiback.

* cited by examiner

FIG. 1

FILM FORMING POLYMERS, METHODS OF USE, AND DEVICES AND APPLICATIONS THEREOF

RELATED APPLICATION

This application is a continuation in part of U.S. patent application Ser. No. 09/537,318, filed Mar. 29, 2000 now abandoned which claims the benefit of Provisional Application No. 60/149,751, filed in the United States Patent and Trademark Office on Aug. 19, 1999, the full disclosures of which are both hereby incorporated by reference herein.

TECHNICAL FIELD

The invention in various embodiments relates to methods and compositions comprising film forming polymers and their applications in pharmaceutics and cosmetics.

BACKGROUND

Transdermal and topical patches have successfully been used as delivery systems, for administering active substances to the humans either systemically or topically. Transdermal delivery methods have been utilized for the systemic treatment of certain disorders as in U.S. Pat. Nos. 5,5152,997; 4,812,313; 4,954,344; and 5,302,395. A transdermal delivery device (patch) containing prostaglandin for the treatment of a pathological condition (e.g. peripheral arterial occlusive disease) is described in U.S. Pat. No. 5,480,648. This patch consists of a pressure sensitive adhesive containing the active component and other additives, laminated onto a backing film. However, the data profile of drug release from this patch as a function of time indicates a process of long term delivery, which is unsuited for the treatment of some conditions for which an effective dose of an active agent is required over a short period of time. Further, a patch for the delivery of active substances, although easy and convenient to use, may present limitations such as sensitization and irritation problems.

SUMMARY

In one embodiment the invention is directed to a composition that includes a mixture of a polymer, an active ingredient, a solvent, and optionally a beneficially acting ingredient capable of being preserved within a container such that on release from the container, the composition forms a peelable, water removable, agent-releasing film on the surface of skin so as to deliver the active ingredient to the skin.

In a further embodiment of the invention, a method for delivering an active agent to the skin of a subject is provided including the steps of mixing at least an active agent and a combination of polymers with a solvent to form a composition; and applying the composition to the skin of the subject for delivery of the active agent to the skin.

DETAILED DESCRIPTION OF SPECIFIC EMBODIMENTS

A new formulation and method for the delivery of active substances to human subjects as a quick drying film forming gel may overcome the problems of slow release, and of sensitization and irritation associated with transdermal topical patches.

In one embodiment, the formulation of the invention includes a film-forming material wherein the film is formed upon application of the formulation to a selected site of the human body. In a preferred embodiment of the present invention the specific formulation can form a film when applied to the skin. The composition can be manufactured as a commercial product in an appropriate device/apparatus for application of the composition to the skin of the subject. The amount of the composition that is delivered by the device to the skin can contain an effective amount of the one or more of the active substances in the composition. The composition may also include a beneficially acting agent that possesses multifunctional properties such as glycerol, lanolin, vaseline, and the like. The film is formed directly on the site of application after the composition is sprayed or otherwise applied, and when dry the gel forms a film on the skin.

The film can be easily removed with water or can be peeled off. Active ingredients to be delivered through such a means can be any of a pharmaceutical or a cosmetic agent. In various embodiments, an active agent can be an anti-inflammatory, a local anesthetic, a xanthine derivative, an antihistaminic, an antifungal, an antimicrobial, an antibiotic, a cardiovascular agent, a hormone, an agent for the treatment of erectile dysfunction, a vasodilator, an analgesic, an antirheumatoid, a chemotherapy agent, an adrenergic agonist or antagonist.

In another embodiment, an active agent in a formulation of the invention can be an antioxidant, a moisturizing agent, an anti-hyperpigmentation agent, an anti-blotching agent, an anti-aging agent, an anti-collagenase substance, a free radical scavenger, a seboregulator, an hydrative, a keratolytic agent and an α-or β-hydroxy acid. A formulation can include a combination of two or more active agents. An ingredient can have multiple different functions in a composition, for example, an emollient such as glycerol can also confer desirable physical properties.

In yet another embodiment, an active agent can be any of a variety of wound healing agents.

The formulations and compositions of this invention can be applied both to the skin and the mucosa.

Definitions

As used in this description and in the accompanying claims, the following terms shall have the meanings indicated unless the context otherwise requires.

An embodiment of the formulation contains a polymer, for example, a polyvinyl alcohol (PVA), for example, a mixture of a first polyvinyl alcohol and a second polyvinyl alcohol of different viscosities. Other biocompatible polymers which are biologically inert polymers include cellulose, carboxymethyl cellulose, PVP/polyvinyl propylene, polyurethane, ethylene vinyl acetate, polyethylene, polypropylene, polystyrene or copolymers thereof (U.S. Pat. No. 5,925,372). A preferred polymer is a polyvinyl alcohol, which confers sufficient viscosity to the composition so that it can form a film, which upon evaporation and concentration of the solvent can form a film that adheres to the skin. In preferred mixtures, a first polyvinyl alcohol having a viscosity in the range of from 38 to 55 cPs is mixed with a second polyvinyl alcohol having a viscosity in the range of from 13 to 27 cPs. The cPs measurements given herein refer to 4% aqueous solution at 20° C. Using the polyvinyl alcohol mixture, it has been found that a second polymer of another type is not required. Nevertheless, additional polymers may be added for use in specific applications. In order to provide a thin, barely visible film, it is preferable to avoid additional polymers. In particular, adhesion promoting polymers such as methacrylate adhesives are not required when using the polyvinyl alcohol mixture. Embodiments using polyvinyl alcohol have shown excellent adhesive properties without additional polymers. In particular, polyvinyl alcohol embodiments have been prepared which produce dry films that require peeling loads of between about 40 to 120 gf. In a particular embodiment, the first polyvinyl alcohol is Mowiol 40-88 and the second polyvinyl alcohol is Mowiol 18-88, both supplied by Clariant GmbH of Sulzbach, Germany. For convenience, a solution or mixture containing the polymer is referred to in the Tables herein as "A". However the methods and processes for preparation of the polymer and other components of the formulations herein are not thereby limited by order of addition or dissolution of ingredients, or by formulation in particular combinations of ingredients, by use herein of this nomenclature.

An "active ingredient" or agent is a substance that presents specific properties used for the treatment of a particular condition. These active agents can be pharmaceutical agents, cosmetics, or wound healing agents.

A "beneficially acting agent" is used mainly in a cosmetic formulation and is not considered to be directed to the treatment of a particular condition, but possesses multifunctional properties that can contribute to the improvement of a condition. For example, glycerol (glycerin) can be included in a moisturizing cream (having a specific moisturizing agent) as an excipient, and in addition the glycerol contributes to and enhances the moisturizing properties of the cream.

An embodiment of the formulation contains an active ingredient or agent, more particularly, a solution or mixture of one or more pharmaceutical, wound healing, and/or cosmetic active ingredients, and can include additional materials such as ethanol, propylene glycol, butylene glycol, and/or other components. The active pharmaceutical ingredients can include an anti-infective, for example, an anti-viral agent, an anti-bacterial agent, an anti-fungal agent, or an anti-parasitical agent. An anti-bacterial agent such as chlorhexidine digluconate, or Triclosan (an antiseptic agent, Irgasan DP 300, Ciba Chemicals), and a salt such as zinc acetate, and other components which can be a pharmaceutical or a cosmetic agent, are listed in the Tables. For the purpose of convenience, the solution or mixture having one or more active ingredients can be referred to as "B" in the Tables and in the text. The method of preparation of the formulations herein are not thereby limited by this designation with respect to order of dissolution or addition of components.

The active ingredient can optionally be formulated in an alcohol-based solvent system, more particularly a lower alkyl alcohol (lower alkanol), for example, methanol, n-propanol, I-propanol, more preferably ethanol, or an alcohol solution or suspension, preferably an ethanol solution or suspension. Active ingredients such as salicylic acid, sodium disulfite, and dl-α-tocopherol can be prepared in the alcohol. For convenience, a formulation can be prepared using only two mixtures or solutions in which the active ingredient in an alcohol solvent is referred to as "B" (see Tables 3, 5, and 7). A single solution can be used, for example an aqueous solution, in which case a designation for the solution or mixture is not given (see Table 6).

One or more hydrophobic substances can be included in the formulation, for example, a formulation to be used in wound healing such as a fumed silica and the like, to modify the release and skin flux characteristics of the formulation system. Other hydrophobic ingredients can be incorporated in the compositions for their multi-functional properties in skin care, for example, Dermacryl 79 (a high molecular weight carboxylated acrylic polymer) by National Starch & Chemical Ltd., U.K., to be used as an effective occlusive agent in the retention of moisture within the skin, and/or to modify the release and skin flux characteristics of the system.

Contained in the formulation embodiments of the present invention can be additives such as solvents, plasticizers, solubilizers, emollients, and preservatives known in the art to be suitable for topical application.

The formulations can be prepared for delivery by use of any of a variety of devices, such as a rollette applicator, a jar having an apical manual pump, an atomizer, or directly from a tube or bottle. A "rollette" applicator is a ball-tipped container such as is commonly used for application of deodorant. A "jar having an apical manual pump" includes a container capable of using compressed air produced by manual depression and release of a movable piston, which imparts to the compressed air a volume of the composition described herein for delivery to the skin of the subject. A "tube" is a compressible delivery container having a cap or cover, such as the ones typically used for the delivery of topically acting active agents in the form of, for example, creams ointments, gels and toothpastes.

Delivery of a controlled dosage of an embodiment of the invention which is a composition can be assisted with an adhesive patch which is a border for a non-patch portion, the non-patch portion having a specific area, for delivery to that specific area of skin. The patch can be of any shape, for example round or rectangular, and the proportion of the border to the non-patch interior is selected by one of skill in the art of design of adhesive patches, to remain in place for a limited period of time following application by any of the devices above. The non-patch interior may have an area of one to 5 sq. cm, or 0.2 to one sq. cm, which are guidelines only and are not to be construed as limiting. The patch is attached to the skin or mucosa of the particular location of skin to be treated, and the composition is applied to the non-patch portion of exposed skin, for example, by spraying or spreading; the patch can be removed when the composition has dried to form a film, or can remain in place.

"Skin" shall mean all of an intact epidermis, a tissue exposed by surgery, a mucosal surface such as an epidermal surface in an oral or vaginal cavity or on a glans penis, and a wound tissue created by abrasion, burn, incision, or a projectile. Cleansing of wounds using a spray has been shown (U.S. Pat. No. 5,059,187), however the spray being delivered as shown in this art was not shown also to form a film. "Mucosa" shall mean the moist epithelial tissues, including for example, the oral or vaginal cavities and glans penis.

Preparation of the Composition

In one embodiment, the preparation of the gel comprises mixing the ingredients designated as B with those designated as A, as so designated in the Tables, under a condition of continuous agitation. To this mixture the ingredients designated as C are added. The preparation is maintained in a sealed container for a period of time, for example, for approximately 6–18 hours, for example, for 12 hours, to allow for removal of the air bubbles. Air bubbles can form and rise to the upper surface of the liquid under conditions of ambient pressure and temperature. Removal of air bubbles from the liquid can be accelerated by application of decreased atmospheric pressure or increased temperature, under conditions of pressure and temperature that are compatible with maintenance of the activity and stability of the composition.

The methods and compositions of the present invention are useful for delivery of one or more of a pharmaceutical agent, for example, an anaesthetic agent, an anti-inflammatory agent such as a glucocorticosteroid and a non-steroidal anti-inflammatory agent (NSAID), or for delivery of one or more of a cosmetic agent, or for delivery of a combination of two or more. pharmaceutical and/or cosmetic agents.

Examples of an anaesthetic agent include Suprane® (desflurane, Ohmeda), Versed® (midazolam hydrochloride, Roche), Duronest® (etidocaine hydrochloride, Astra), Naropin® (ropivacaine hydrochloride) Nesacaine® (chloroprocaine hydrochloride), and Xylocaine® (lidocaine hydrochloride). Base forms of the anaesthetic agents can be incorporated into a composition, for example, lidocaine base in Example 11 herein.

Examples of a glucocorticosteroid agent include Celestone® (betamethasone sodium, Schering), Cortone® acetate (cortisone acetate, Merck), Decadron® (dexamethasone sodium phosphate, Merck), and Hydrocortone® (hydrocortisone, Merck).

Examples of an NSAID agent include Toradol® (ketorolac tromethamine, Roche), Cataflam® (diclofenac potassium), Clinoril® (sulindac, Merck), Indocin® (indomethacin sodium trihydrate, Merck), and Lodine® (etodolac, Wyeth-Ayerst).

A cosmetic agent can include, for example, an anti-irritant such as: α-bisabolol, camomile extract, tea tree (*Melaleuca alternifolia*) oil, green tea (*Camellia sinensis*) extract, aloe (*Aloe vera*) extract (NOVA; see Examples 1–6), licorice (*Glycerrhiza glabra*) extract, glycyrrhetinic acid, witch hazel (*Hamamelis virginiana*) extract, and glycerol. Green tea and other plant material extracts can be obtained, for example, in solution with propylene glycol and water, for example, Optivegetol Green Tea P108 Hydro, Gattefosse (France); Optivegetol Cinnamon (*Cinnamomum cassia*) P110 Hydro, Gattefosse; and Optivegetol Guarana (*Paullinia cupana*) P107 Hydro, Gattefosse. Optivegetol green tea hydroglycollic extract possesses anti-inflammatory and anti-irritant properties.

Examples of anti-infective agents include: anti-viral, anti-bacterial, anti-fungal and anti-parasitic agents. Anti-bacterial agents include chlorhexidine and Triclosan. Anti-infectives may further include antiseptic agents. Examples of an antiseptic agent include: an alcohol such as a lower alkyl alcohol including ethyl alcohol and isopropyl alcohol. Other antiseptic agents include phenyl alcohol, tea tree oil, iodine compounds such as povidone iodide, and mercurichrome.

Examples of an antioxidant agent are propyl gallate, sodium bisulfite, ascorbic acid (vitamin C) and ascorbic acid esters, butylated hydroxytoluene (BHT), butylated hydroxyanisole (BHA), vitamin E, and cysteine.

Examples of a vitamin include: vitamin A, vitamin A palmitate, β-carotene, ascorbic acid (vitamin C), ascorbyl palmitate, tocopherol (vitamin E), tocopheryl acetate (vitamin E acetate), vitamin K, and vitamin F (glyceryl linoleate and glyceryl linolenate).

Examples of a skin-conditioning ingredient include: extract of any of aloe (for example, *Aloe vera*), *Camellia sinensis* (green tea), camomile, cucumber, corn flower, orange peel, dog rose hip; marine extracts such as those from seaweed, kelp, and algae; rice bran oil, wheat germ oil, avocado oil and almond oil; an β-hydroxy acid (AHA) such as glycolic acid, lactic acid, malic acid, and citric acid; a β-hydroxyl acid such as salicylic acid, a polymeric hydroxylic acid, and a ketoacid; and a β-glucan, panthenol, an anthocyanidin, a phytic acid, and an amino acid such as glycine, proline, lysine and leucine.

In embodiments of the present invention, a cosmetic active agent known in the art may be incorporated in the film forming compositions for improving skin appearance. These agents can be any of anti-hyperpigmentation, anti-blotching, anti-aging, eye contour, slimming, anti-cellulite, soothing/sunburn, anti-irritating, skin firming and lifting, anti-elastase and anti-collagenase substances, free radical scavengers, seboregulators, hydratives, vitamins, AHA products, anti-oxidants and minerals.

Anti-hyperpigmentation agents typically used for counterbalancing this condition can include tyrosinase inhibitors such as peptide mixtures and plant extracts, fermentation products, and antioxidants such as hydroquinone (see Examples 7–8), kojic acid (see Example 9), ascorbic acid derivatives, synthetic or natural derivatives of hydroquinone and hydroquinone precursors. Gatuline whitening obtained by fermentation of kojic and lactic acids, is a tyrosinase inhibitor. In preferred embodiments of the invention, anti-hyper pigmentation agents are Melawhite of Pentharm Ltd., Basel, Switzerland; Biowhite™ of Coletica, France; Etioline of Sederma, France; Arbossa of Kelesima, Italy; Gatuline whitening of Gattefosse, France; Ascorbocilan C of Exsymol, Monaco; and Kojic acid of Alps Pharm., Japan.

Anti-blotching agents typically used for counterbalancing this condition can include saponines and caffeic acid containing plant extract and related compounds. Preferably in the present invention, anti-couprose agents include Gatuline A of Gattefosse, France, and Ivy-Phytelenes of Sepex, France.

Anti-aging agents include glycosaminoglycan derivatives such as chondroitin sulfate and ATP; other bioactivators such as farnesol and farnesol derivatives; panthenol and panthenol derivatives; beech tree bud extracts; and soya bean embryonic tissue extracts and related compounds. Preferably in the present invention, anti-aging agents are Unichodrin ATP and Unitrienol T-27 (Induchem, Switzerland), and Gatuline RC (Gattefosse, France).

Skin firming and lifting agents include a mixture of plant protein fractions, flavonoids and tannins such as Gatuline Lifting of Gattefosse, France.

Keratolytic agents include salicylic acid, benzoyl peroxide, sulfur, retinoic acid, and any of several fruit acids.

Free radical scavengers include synthetic pseudopeptides resistant to hydrolysis such as Carcinine hydrochloride; lipoamino acids such as L-lysine lauroylmethionine; plant extracts containing multi-enzymes; and natural tocopherol and related compounds. In a preferred embodiment of the invention, free radical scavengers are Alistin of Excymol, France, Lipacide LML of Seppic, France, and Radicallne® of Coletica, France.

Seboregulators include lipoamino acids of natural origin such as capryloyl glycine; oxidative enzyme mixtures; and mixtures of hydrolyzed yeast proteins and vitamins and related compounds. In a preferred embodiment of the invention, seboregulators are Asebiol® BT of Laboratoires Serobiologiques, France; Lipacide C8G of Seppic, France; Sebomine/SB12 of Sederma, France; and Biomeris of Biopole, Belgium.

AHA specific products can be mono-, di-, tri-hydroxy acids of natural origin, which may further be linked to polysaccharides or proteins. In a preferred embodiment of the invention, AHA specific products are Glycacid® and Protacid® of Coletica, France; Multifruit® BSC of Brooks Industries Inc., USA; Amidroxy of Alban Mulle Int., France; and AHA extracts of Phytochim, France.

Additional agents that can be present in the compositions of embodiments herein include Crolastine 30 which contributes to elasticity of the skin, Hygrocomplex ARO which is a moisturizing agent, Crodalan (Croda, England), and Biopure 100 which is a preservative (see Table 1).

EXAMPLES

Delivery

Each formulation can be sprayed upon the skin by any of the methods known in the art, for example, delivering a measured dose using a spray container (see U.S. Pat. Nos. 5,618,515 and 5,769,283) as an atomizer attached to a reservoir, or for example, a pump inserted into the aqueous solution such that removal of a restraining cap enables use of first and second fingers to stabilize the vessel containing the reservoir while pushing with the thumb causes delivery of the measured dose. Use of an atomizer does not require pressurization of an additional gas component. The geometry of the relationship of the pump and the reservoir containing the gel can be of standard description, for example, a separate squeezable pump removably attached to one side, or a top pump which is activated by a push mechanism.

Formulations may be applied to the skin in measured doses or less precisely. In addition to the more carefully controlled delivery devices just described, formulations can be applied from a rollette or tube container. Alternatively, the formulations can be provided as separate doses in solid discs of the formulation that become spreadable gels when water is added.

The moist formulation, however applied, is allowed to dry on the skin. A peelable, water-removable, agent-releasing film is thus formed. The thickness of the film is between 0.01 to 0.25 mm, preferably between 0.03 and 0.10 mm. Typically, the film is at least translucent to reduce its visibility on the skin. The film may appear like a thin flaky layer of parchment. In preferred embodiments, the film is transparent.

The dosage of active agent is delivered to the skin over time from the moist formulation and then from the dry film. In preferred embodiments, the active agent is percutaneously absorbed through the skin. Thus, the dry film can be effectively used as drug delivery system for delivering a controlled dose of a drug over time.

Ranges of Components

Mixture or solution A can comprise a first polyvinyl alcohol (having viscosity in the range of from 38 to 55 cPs) in a range from 5 to 10% amount, on a wet basis, with respect to the total composition. This component is preferably present at less than 20%, more particularly 1–10%, more particularly from 6 to 8%, more preferably from 6.9 to 7.5%, on a wet basis, with respect to the total composition. A second polyvinyl alcohol (having viscosity in the range of from 13 to 27 cPs) is present at less than 20%, more particularly 1–10%, more particularly from 3.5 to 6.0%, preferably from 4.0 to 5.0%, more preferably from 4.5 to 4.8%, on a wet basis, with respect to the total composition. The ratio of first polyvinyl alcohol to second polyvinyl alcohol is about 3:2.

Mixture or solution B can comprise a number of ingredients, including at least one active agent and a solvent system which may include water. Humectant ingredients which are miscible with water, such as propylene glycol can be added, as can other solvents such as ethanol. Examples of active ingredients in B are found in Tables 1 and 2. Active ingredients can be present, on a wet basis, with respect to the total composition, in amounts from 0.01 to 20%, for example, from 0.1 to 6%.

Mixture or solution C can comprise an alcohol of a lower alkyl (a lower alkanol), for example, methanol, n-propanol, I-propanol, preferably ethanol, and one or more additional ingredients, which preferably are more soluble in ethanol compared to water. The alcohol can also be present from 1 to 20% on a wet basis, with respect to the total composition. The alcohol, preferably ethanol, is preferably present at 8 to 18%, 10 to 16%, most preferably 12 to 17%, on a wet weight basis with respect to the total composition. An active ingredient soluble in the alcohol such as hydroquinone, salicylic acid, and/or dl-α-tocopherol, can also be present in C. The active ingredient in C can be present from 0.01 to 10%, preferably 0.1 to 1%, on a wet basis, with respect to the total composition.

Examples 1–32

Formulations of Active Components in Film Forming Polymers

The cosmetic formulations of Examples 1–6 are shown in Table 1, and formulations containing anti-pigmentation agents are shown in Examples 7–9 in Table 2. Except for Example 9, all of the components are mixed as described above.

Examples 7–9 (Table 2) are formulations of the invention having anti-pigmentation agents. Examples 7 and 8 contain hydroquinone, which can be applied topically as a depigmenter agent (Merck Index, Tenth Ed., 1983, Rahway, N.J.). The formulation for Example 9 contains anti-pigmentation agents Melfade™, GATULINE® whitening, Kojic acid, and Biowhite™. A formulation for treating age spots, for example on the hands, face, shoulders, chest or neck, is shown in Example 10 (Table 3). The methods and compositions that are gel forming polymers are particularly suitable for application to a limited surface area of skin such as an age spot.

The invention in another embodiment is a formulation containing a local anesthetic (Example 11, Table 4), for example, the anesthetic lidocaine. In yet another embodiment, the invention provides a formulation containing an anti-histaminic agent, hydroxyzine (Examples 12–15, Table 5). The methods and compositions of the invention are suitable to treatment of areas of skin having an inflammation or irritation, such as an allergic contact dermatitis, or a reaction to an insect bite, by application of a film-forming gel having a water soluble polymer and containing an active agent such as an anesthetic or antihistamine.

The compositions of the invention can include an animal protein hydrolysate, for example, a collagen extract, as a skin conditioning agent (Examples 16–19, Table 6).

An anti-acne formulation can combine one or more of each of an anti-irritant, antibacterial agent, and a keratolytic agent such as salicylic acid (Examples 20–22, Table 7). Additional formulations (Examples 23–29) are shown in Table 8, the formulations having an anti-bacterial agent such as chlorhexidine, triclosan, or both. Additional formulations of Examples 30–32 are shown in Table 9.

TABLE 1

Compositions of cosmetic formulations for Examples 1–6

| | | % Amount (on a wet basis) | | | | | |
|---|---|---|---|---|---|---|---|
| Mix | Component | Ex. 1 | Ex. 2 | Ex. 3 | Ex. 4 | Ex. 5 | Ex. 6 |
| A | 1st Polyvinyl alcohol (Mowiol 40-88) | 7.04 | 7.30 | 7.30 | 7.30 | 6.99 | 7.30 |
| | 2nd Polyvinyl alcohol (Mowiol 18-88) | 4.53 | 4.70 | 4.70 | 4.70 | 4.50 | 4.70 |
| | Deionized water | 58.05 | 54.20 | 52.20 | 58.20 | 57.61 | 60.20 |
| B | Aloe vera gel NOVA[1] | 1.93 | 2.00 | 2.00 | 2.00 | 1.91 | |
| | Crolastine 30[2] | | | | | | 2.00 |
| | Deionized water | 6.22 | 6.45 | 6.45 | 6.45 | 6.17 | 6.25 |
| | Propylene glycol | | | | | | 4.00 |
| | Hygrocomplex ARO[3] | | | | | | 2.00 |
| | Crodalan[5] | | | | | | 0.20 |
| | Butylene glycol | | 4.00 | 4.00 | 4.00 | | |
| | Chlorhexidine digluconate | 0.19 | 1.00 | 1.00 | 1.00 | 0.96 | |
| | Optivegetol[4] | 5.79 | 6.00 | 6.00 | | 5.74 | |
| | Zinc acetate | | | 2.00 | 2.00 | | |
| | Biopure 100[6] | 0.24 | 0.25 | 0.25 | 0.25 | 0.24 | 0.25 |
| C | Nipagin M[7] | 0.10 | 0.10 | 0.10 | 0.10 | 0.10 | 0.10 |
| | Salicylic acid | 0.96 | 1.00 | 1.00 | 1.00 | 0.96 | |
| | Ethanol absolute | 14.95 | 13.00 | 13.00 | 13.00 | 14.83 | 13.00 |

[1]Aloe vera gel NOVA, a juice (gel) from fresh leaves of the Aloe vera plant, possesses anti-inflammatory and anti-irritant properties.
[2]Crolastin 30 is a hydrolyzed elastin, contributing to elasticity of the skin.
[3]Hygrocomplex ARO, a mixture of specific amino acids, forms a natural moisturizing factor (NOVAROM, Hannover, Germany).
[4]Optivegetol, a hydroglycolic extract of green tea leaves, has free radical scavenging, antioxidant, and vitamin P properties (Gattefosse, France).
[5]Crodalan is a multi-functional surface active emollient (Croda, England).
[6]Biopure 100 (imidazolidine urea) is a preservative for cosmetic and dermopharmaceutical formulations (NIPA Lab, U.K.).
[7]Nipagin M, a methyl 4-hydroxybenzoate solution, is used as preservative (NIPA Lab, U.K.).

TABLE 2

Compositions for Examples 7–9 containing anti-pigmentation agents

| | | % Amount (on a wet basis) | | |
|---|---|---|---|---|
| Mix | Component | Ex. 7 | Ex. 8 | Ex. 9 |
| A | 1st Polyvinyl alcohol (Mowiol 40-88) | 7.50 | 7.50 | 7.30 |
| | 2nd Polyvinyl alcohol (Mowiol 18-88) | 4.70 | 4.70 | 4.70 |
| | Sodium disulphite | 0.10 | | |
| | Melfade ™[1] | | | 5.00 |
| | Deionized water | 58.80 | 56.80 | 55.90 |
| B | Aloe vera gel | 2.00 | 2.00 | |
| | Deionized water | 6.45 | 6.45 | |
| | Propylene glycol | 4.00 | | |
| | Optivegetol | | 6.00 | |
| | Biopure 100 | 0.25 | 0.25 | |
| | GATULINE ® whitening[2] | | | 5.00 |
| | Kojic acid | | | 1.00 |
| | Biowhite ™[3] | | | 0.10 |
| | Eutanol G16S | | | 2.00 |
| | Butylene glycol | | | 2.00 |
| | Nipagin M | | | 0.10 |
| | Ethanol absolute | | | 16.90 |
| C | Nipagin M | 0.10 | 0.10 | |
| | Oxynex 2004[4] | 0.10 | 0.10 | |
| | Sodium disulphite | | 0.10 | |
| | dl-α-tocopherol | 1.00 | 1.00 | |
| | Hydroquinone | 2.00 | 2.00 | |
| | Ethanol absolute | 13.00 | 13.00 | |

[1]Melfade ™ is a tyrosinase inhibitor by Pentharm, Basel, Switzerland.
[2]GATULINE ® whitening is a tyrosinase inhibitor containing a fraction obtained by fermentation (kojic acid and lactic acid), licorice extract, and TRANSCUTOL ® (Gattefosse, France).
[3]Biowhite ™ is a tyrosinase inhibitor (Coletica, France).
[4]Oxynex 2004 is an antioxidant mixture used in pharmaceuticals, containing 20% butyl hydroxy toluene, 10% ascorbic acid, and 10% citric acid in glyceryl stearate and propylene glycol (E. Merck, Germany).

TABLE 3

A composition of Example 10 containing anti-aging spot agents

| Mix | Component | % Amount (on a wet basis) |
|---|---|---|
| A | 1st Polyvinyl alcohol (Mowiol 40-88) | 7.50 |
| | 2nd Polyvinyl alcohol (Mowiol 18-88) | 4.70 |
| | Sodium disulphite | 0.10 |
| | Deionized water | 58.80 |
| B | Aloe vera gel | 2.00 |
| | Deionized water | 6.45 |
| | Propylene glycol | 4.00 |
| C | Nipagin M | 0.10 |
| | Oxynex 2004 | 0.10 |
| | dl-α-tocopherol | 1.00 |
| | Hydroquinone | 2.00 |
| | Ethanol absolute | 13.00 |

TABLE 4

A composition of Example 11 containing a local anesthetic

| Mix | Component | % Amount (on a wet basis) |
|---|---|---|
| A | 1st Polyvinyl alcohol (Mowiol 40-88) | 7.3 |
|   | 2nd Polyvinyl alcohol (Mowiol 18-88) | 4.7 |
|   | Deionized water | 62.1 |
| B | Propylene glycol | 5.0 |
|   | Lidocaine base | 5.0 |
|   | Ethanol absolute | 15.9 |

TABLE 5

Compositions containing hydroxyzine hydrochloride (antihistaminic) of Examples 12–15

| | | % Amount (on a wet basis) | | | |
|---|---|---|---|---|---|
| Mix | Component | Ex. 12 | Ex. 13 | Ex. 14 | Ex. 15 |
| A | 1st Polyvinyl alcohol (Mowiol 40-88) | 7.3 | 7.3 | 7.3 | 7.3 |
|   | 2nd Polyvinyl alcohol (Mowiol 18-88) | 4.7 | 4.7 | 4.7 | 4.7 |
|   | Deionized water | 65.9 | 51.0 | 51.0 | 51.0 |
| B | Hydroxyzine HCl | 5.0 | 5.0 | 5.0 | 5.0 |
|   | Linoleic acid | | | | 5.0 |
|   | Montane 80 VGA | | | 5.0 | |
|   | Eutanol G16S | | 5.0 | | |
|   | Butylene glycol | 4.0 | 10.0 | 10.0 | 10.0 |
|   | Nipagin M | 0.1 | 0.1 | 0.1 | 0.1 |
|   | Ethanol absolute | 13.0 | 16.9 | 16.9 | 16.9 |

TABLE 6

Compositions of Examples 16–19 containing collagen

| | % Amount (on a wet basis) | | | |
|---|---|---|---|---|
| Component | Ex. 16 | Ex. 17 | Ex. 18 | Ex. 19 |
| 1st Polyvinyl alcohol (Mowiol 40-88) | 7.3 | 7.3 | 7.3 | 7.3 |
| 2nd Polyvinyl alcohol (Mowiol 18-88) | 4.7 | 4.7 | 4.7 | 4.7 |
| Deionized water | 72.98 | 74.98 | 74.97 | 75.58 |
| Hydrolyzed collagen[1] | 0.6 | 0.6 | 0.6 | 0.2 |
| Glycerol | 2.0 | 2.0 | 2.0 | |
| Potassium sorbate | 0.12 | 0.12 | 0.12 | 0.12 |
| Germal II[2] | 0.3 | 0.3 | 0.3 | 0.3 |
| MEM-EARL[3] | 12.0 | 10.0 | 10.0 | 10.0 |
| Benzalkonium chloride | | | | 0.1 |

[1]Hydrolyzed collagen is a collagen extract used as a skin conditioning agent (Croda, Inc.).
[2]Germal II is diazolidinyl urea preservative (ELTON, Greece).
[3]MEM-EARL is a tissue culture medium (Sigma, St. Louis, MO).

TABLE 7

Compositions of Examples 20–22 containing anti-acne agent salicylic acid

| | | % Amount (on a wet basis) | | |
|---|---|---|---|---|
| Mix | Component | Ex. 20 | Ex. 21 | Ex. 22 |
| A | 1st Polyvinyl alcohol (Mowiol 40-88) | 6.89 | 7.3 | 7.3 |
|   | 2nd Polyvinyl alcohol (Mowiol 18-88) | 4.43 | 4.7 | 4.7 |
|   | Deionized water | 60.57 | 53.2 | 61.7 |
| B | Aloe vera gel NOVA | 1.89 | 2.0 | 2.0 |
|   | Deionized water | 6.08 | 6.45 | 6.45 |
|   | Butylene glycol | | 4.0 | |
|   | Chlorhexidine digluconate | 0.94 | 1.0 | 1.0 |
|   | Optivegetol | 5.66 | 6.0 | |
|   | Biopure 100 | 0.24 | 0.25 | 0.25 |
| C | Nipagin M | 0.09 | 0.1 | 0.1 |
|   | Salicylic acid | 0.94 | 1.0 | 1.0 |
|   | Ethanol absolute | 12.26 | 13.0 | 15.5 |

TABLE 8

Compositions of Examples 23–29 containing anti-bacterial agents

| | | % Amount (on a wet basis) | | | | | | |
|---|---|---|---|---|---|---|---|---|
| Mix | Component | Ex. 23 | Ex. 24 | Ex. 25 | Ex. 26 | Ex. 27 | Ex. 28 | Ex. 29 |
| A | 1st Polyvinyl alcohol (Mowiol 40-88) | 6.91 | 6.98 | 7.01 | 7.12 | 6.88 | 6.87 | 6.85 |
|   | 2nd Polyvinyl alcohol (Mowiol 18-88) | 4.45 | 4.49 | 4.51 | 4.58 | 4.43 | 4.42 | 4.41 |
|   | Deionized water | 56.95 | 57.54 | 57.83 | 58.73 | 56.73 | 56.67 | 56.45 |
| B | Aloe vera gel NOVA | 1.89 | 1.91 | 1.92 | 1.95 | 1.88 | 1.88 | 1.88 |
|   | Deionized water | 6.10 | 6.16 | 6.20 | 6.29 | 6.08 | 6.07 | 6.05 |
|   | Butylene glycol | 1.89 | 1.91 | 1.92 | 1.95 | 1.88 | 1.88 | 1.88 |
|   | Chlorhexidine digluconate | 1.49 | 1.51 | 1.52 | | 1.49 | 1.49 | 1.48 |
|   | Glycerol | | | | | 1.88 | 1.88 | 1.88 |
|   | Biopure 100 | 0.24 | 0.24 | 0.24 | 0.24 | 0.24 | 0.24 | 0.23 |

TABLE 8-continued

Compositions of Examples 23–29 containing anti-bacterial agents

| Mix | Component | % Amount (on a wet basis) | | | | | | |
|---|---|---|---|---|---|---|---|---|
| | | Ex. 23 | Ex. 24 | Ex. 25 | Ex. 26 | Ex. 27 | Ex. 28 | Ex. 29 |
| C | Nipagin M | 0.10 | 0.11 | 0.11 | 0.11 | 0.10 | 0.10 | 0.10 |
| | Glycyrrhetinic acid | | | | | | 0.10 | |
| | Salicylic acid | 2.01 | 1.00 | 0.50 | 0.50 | 0.50 | 0.50 | 1.00 |
| | Triclosan | 0.30 | 0.31 | 0.31 | 0.31 | 0.30 | 0.30 | 0.30 |
| | Montane 80 VGA | 2.50 | 2.52 | 2.54 | 2.58 | 2.49 | 2.49 | 2.48 |
| | Bisabolol | 0.50 | 0.51 | 0.51 | 0.52 | 0.50 | 0.50 | 0.50 |
| | Ethanol absolute | 14.67 | 14.81 | 14.89 | 15.12 | 14.61 | 14.59 | 14.53 |

TABLE 9

Compositions of Examples 30–32 containing anti-bacterial agents

| Mix | Component | % Amount (on a wet basis) | | |
|---|---|---|---|---|
| | | Ex. 30 | Ex. 31 | Ex. 32 |
| A | 1st Polyvinyl alcohol (Mowiol 40-88) | 6.84 | 6.74 | 6.64 |
| | 2nd Polyvinyl alcohol (Mowiol 18-88) | 4.40 | 4.34 | 4.27 |
| | Deionized water | 56.39 | 55.60 | 54.74 |
| B | Aloe vera gel NOVA | 1.87 | 1.85 | 1.82 |
| | Deionized water | 6.04 | 5.96 | 5.86 |
| | Butylene glycol | 1.87 | 1.85 | 1.82 |
| | Chlorhexidine digluconate | 1.48 | 1.46 | 1.44 |
| | Glycerol | 1.87 | 1.85 | 1.82 |
| | Biopure 100 | 0.23 | 0.23 | 0.23 |
| C | Nipagin M | 0.10 | 0.10 | 0.10 |
| | Dermacyl 79 | | 1.50 | 3.00 |
| | Glycyrrhetinic acid | 0.10 | | |
| | Salicylic acid | 1.00 | 0.49 | 0.50 |
| | Triclosan | 0.30 | 0.30 | 0.29 |
| | Montane 80 VGA | 2.47 | 2.44 | 2.40 |
| | Bisabolol | 0.50 | 1.00 | 0.98 |
| | Ethanol absolute | 14.52 | 14.31 | 14.09 |

Example 33

Pre-Clinical Data Showing Efficacy of Formulations to Heal Acne Symptoms

The efficacy of formulations of the present application was tested on volunteer humans aged 20 to 34 years. The formulations investigated were those of Examples 28, 29, 30 and 31, respectively.

Using an appropriate applicator system, each formulation was applied exclusively at the site of an inflamed area (the acne-related inflammation) of the face, and remained in place overnight. Application was repeated on each of subsequent nights, until complete healing was observed.

The results in the following tables are given as the percentage of subjects cured as a function of time, expressed as the number of nights of use. The effectiveness of each of the formulations was evaluated using the following criteria: increase in dryness of the inflamed area, reduction of erythema, and reduction of edema.

TABLE 10

Effect on dryness (significant improvement)

| Application: | first | second | third | fourth |
|---|---|---|---|---|
| Example 27 | | 50 | 50 | |
| Example 28 | | 20 | 20 | 60 |
| Example 29 | | | | 100 |
| Example 30 | 34 | 66 | | |

TABLE 11

Reduction of inflammation (significant improvement)

| Application | first | second | third | fourth |
|---|---|---|---|---|
| Example 27 | | 50 | 50 | |
| Example 28 | 40 | | 60 | |
| Example 29 | | 100 | | |
| Example 30 | | | | 66* |

*Moderate improvement. One subject did not complete the study

TABLE 12

Reduction of edema (significant improvement)

| Application | first | second | third | fourth |
|---|---|---|---|---|
| Example 27 | 50 | 50 | | |
| Example 28 | 20 | 20 | 40 | |
| Example 29 | | 100 | | |
| Example 30 | 66* | | | |

*One subject did not complete the study

Tables 10–12 show that each of the formulations of Examples 28–31, when applied using the methods of the invention to form a gel to deliver the active agents to the skin of the subject, was effective as an anti-acne formulation, by the three criteria of increasing the dryness, reducing erythema (redness), and reducing edema (swelling), within four nights of use. Some of these formulations successfully met one or two of the criteria after only two to three nights of use. The formulation of Example 28 eliminated inflammation and edema after two nights, and provided a dry area after three nights of use. The formulation of Example 33 eliminated edema after one night, produced dry skin after two nights, and reduced inflammation after the fourth night of use.

Example 34

Evaluation of the Formulations Using a Depletion Analysis

Formulations herein were evaluated for capacity to release active substances as a function of time after topical application to human skin. To determine the rate and extent of release of an active component of compositions of the formulations, a patch depletion analysis was performed. Among formulations of embodiments of the invention herein, those of Examples 24, 25, and 31 were tested.

An appropriate amount of each composition was applied to the hand (covering the upper side), and dried to form a film. At 45 and 120 minutes post application, a portion of the film was removed using forceps, and the amount of active components was determined by employing HPLC-based analytical procedures.

The results shown in the Table 13 express the percent of salicylic acid remaining in the patch sample, calculated from comparison to the amount at time zero (100%). The data demonstrate that the amount of salicylic acid in the film patch decreases as a function of time that the film of each of formulations has been in contact with skin of the hand.

These data indicate that significant amounts of the original content of the active agent was depleted from the composition during the time that the dry film was in contact with the skin, since the depleted amount increased as a function of time. In this test, the formulation of Example 31 delivered a greater proportion of the active component to the skin of the human hand than the other formulation during an application period of 2 hours.

TABLE 13

Depletion of active ingredient from gel patches as a function of time of skin contact

| Formulation | Time of sample (min) | salicylic acid remaining (%) |
|---|---|---|
| Example 24 | 45 | 61.1 |
|  | 120 | 51.9 |
| Example 25 | 45 | 67.5 |
|  | 120 | 66.0 |
| Example 31 | 45 | 71.6 |
|  | 120 | 44.1 |

Example 35

Evaluation of Percutaneous Absorption Using Formulations

To evaluate any local effect induced by the use of the formulations, the absorption (flux) of active component salicylic acid from the formulation shown in Table 14, was determined in vitro by using human cadaver skin by the method of Franz, T. (Percutaneous absorption on the relevance of the in vitro data, J. Invest. Derm. 64:190–195 (1975)). For these in vitro flux studies, stratum corneum samples of human skin obtained from fresh post-mortem cadaver autopsy was used. Samples of stratum corneum were separated according the Kligman, A. M. et al. (Preparation of the isolated sheets of the human stratum corneum, Arch. Derm. 88:702 (1963)). The formulation of Table 14 was pre-dried to form a film prior to application onto the Frantz device, having an area of 0.639 cm$^2$. Another aliquot of same amount of the formulation was placed in liquid form onto the surface of the cell in the Frantz device.

Figure 1:
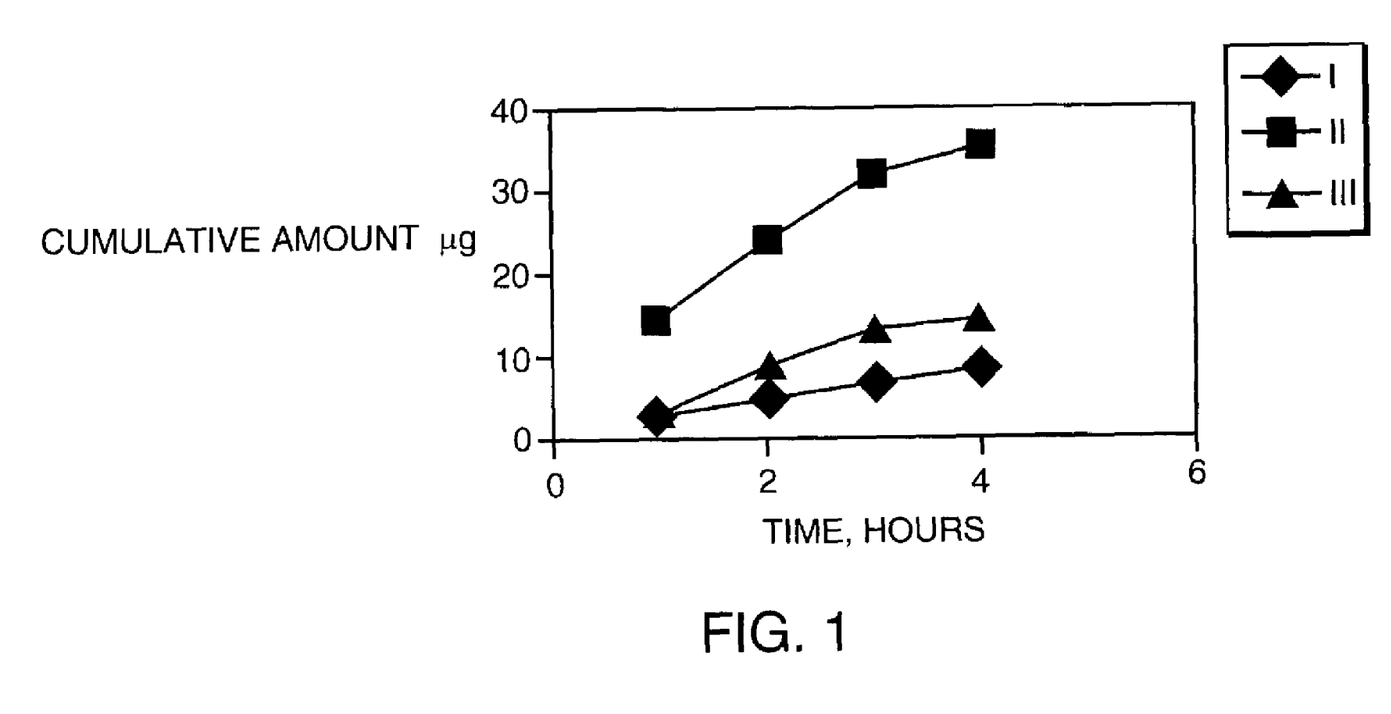
FIG. 1 is a graph showing on the ordinate the cumulative amount of active component absorbed percutaneously by human stratum corneum, in p g, and on the abscissa the time in hours that the sample was taken for analysis following application to the skin, formulated in (I) a commercial product (SYNERGIE patch containing 0.73% salicylic acid, Lavipharm S.A. for Garnier, France; (II) a dry film produced by a formulation applied and dried in situ containing 3.23% salicylic acid; and (III) the formulation identical to (II) applied as a liquid.

Observation of the skin flux (percutaneous absorption) for each sample at each time point (expressed as cumulative amount of salicylic acid permeation per unit of area at any given time) was compared as a function of time in each of the following compositions: (I) commercial product (SYNERGIE patch from Lavipharm S.A., for Gamier, France) containing salicylic acid as active ingredient, 0.73% w/w on a dry basis; (II) a dry film of the formulation in Table 14; and (III) the identical liquid formulation of Table 14 before dryness, both II and III containing the same amount of salicylic acid, 3.23% w/w on a dry basis.

The results (FIG. 1) show that significant amounts of the active component permeated into the stratum corneum. The greatest flux of the active component was observed with use of the dry gel (II in FIG. 1), a formulation which is an embodiment of the invention.

TABLE 14

Formulation for percutaneous absorption study of Example 35

| Mix | Component | % Amount (on a wet basis) |
|---|---|---|
| A | 1$^{st}$ Polyvinyl alcohol (Movwiol 40-88) | 6.87 |
|  | 2$^{nd}$ Polyvinyl alcohol (Mowiol 18-88) | 4.42 |
|  | Deionized water | 56.62 |
| B | Aloe vera gel NOVA | 1.88 |
|  | Deionized water | 6.07 |
|  | Butylene glycol | 1.88 |
|  | Chlorhexidine digluconate | 1.49 |
|  | Glycerol | 1.88 |
|  | Biopure 100 | 0.24 |
| C | Nipagin M | 0.10 |
|  | Salicylic acid | 0.70 |
|  | Triclosan | 0.30 |
|  | Montane 80 VGA | 2.48 |
|  | Bisabolol | 0.50 |
|  | Ethanol absolute | 14.67 |

What is claimed is:

1. A formulation, comprising: an aqueous mixture including a first polyvinyl alcohol having a viscosity in the range of from 38 to 55 cPs, a second polyvinyl alcohol having a viscosity in the range of from 13 to 27 cPs and at least one active agent selected from a pharmaceutical agent, a wound healing agent and a cosmetic agent, but not containing adhesion-promoting polymers other than polyvinyl alcohol, the mixture forming a composition, the composition when dried forming an agent releasing, water removable, peelable film when applied to a skin surface.

2. A formulation according to claim 1, wherein the pharmaceutical agent is an agent selected from the group consisting of: an anti-inflammatory, a local anesthetic, a xanthine derivative, an antihistaminic, an antifungal, an antimicrobial, an antibiotic, a cardiovascular, a hormone, an erectile dysfunction treatment, a vasodilator, an antirheumatoid, a chemotherapy, an adrenergic agonist or an adrenergic antagonist.

3. A formulation according to claim 1, wherein one or more cosmetic agents are selected from the group consisting of: anti-irritant, anti-oxidant, skin conditioning, anti-blotching, anti-aging, anti-cellulite, skin firming, eye contour, slimming, sooth, sunburn, skin lifting, anti-elastase, anti-collagenase, free radical scavenger, seboregulator, hydrative, vitamin, mineral, a-hydroxy acid, and anti-hyperpigmentation agents.

4. A formulation according to claim 1, wherein the composition is in the form of a gel.

5. A formulation according to claim 1, wherein the first polyvinyl alcohol and second polyvinyl alcohol are present at about 6 to 8% and 4 to 5%, respectively, on a wet weight basis with respect to the total composition.

6. A formulation according to claim 1, wherein the ratio of first polyvinyl alcohol to second polyvinyl alcohol is about 3:2.

7. A formulation according to claim 1 wherein the film is at least translucent.

8. A formulation according to claim 7 wherein the film is transparent.

9. A formulation according to claim 1 wherein the film is between 0.01 and 0.25mm thick.

10. A formulation according to claim 1 wherein the film is 0.03 to 0.1mm thick.

11. A method for administering a dosage of at least one active agent to a site on a subject, comprising:
  (i) providing a formulation, the formulation including a first polyvinyl alcohol having a viscosity in the range of from 38 to 55 cPs, a second polyvinyl alcohol having a viscosity in the range of from 13 to 27 cPs, water and at least one active agent selected from one or more of a pharmaceutical agent, a wound healing agent and a cosmetic agent;
  (ii) releasing from a container, a quantity of the formulation onto skin of the subject so as to form a quick-drying, agent releasing, water removable, peelable film capable of overnight adhesion and containing the active agent, wherein polymers contributing to said overnight adhesion consist of the first and second polyvinyl alcohols; and
  (iii) a administering the agent to the subject from the film.

12. A method according to claim 11, wherein the first polyvinyl alcohol and the second polyvinyl alcohol, each present at about 1 to 10%, on a wet weight basis with respect to the total composition.

13. A method according to claim 11, wherein the first polyvinyl alcohol and the second polyvinyl alcohol are present at about 6 to 8% and 4 to 5%, respectively, on a wet weight basis with respect to the total composition.

14. A method according to claim 11, wherein at least one agent is selected from the group consisting of: an anti-inflammatory, a local anesthetic, a xanthine derivative, an antihistaminic, an antifungal, an antimicrobial, an antibiotic, a cardiovascular, a hormone, an erectile dysfunction treatment, a vasodilator, an antirheumatoid, a chemotherapy, an adrenergic agonist, an adrenergic antagonist, an anti-irritant, an anti-oxidant, a skin conditioning, an anti-blotching, an anti-aging, an anti-cellulite, a skin firming, a eye contour, a slimming, a sunburn soothing, a skin lifting, an anti-elastase, an anti-collagenase, a free radical scavenger, a seboregulator, a hydrative, a vitamin, a mineral, an a-hydroxy acid, and an anti-hyperpigmentation agents.

15. A method according to claim 11 wherein the film is at least translucent.

16. A method according to claim 15 wherein the film is transparent.

17. A method according to claim 11 wherein the film is between 0.01 and 0.25 mm thick.

18. A method according to claim 11 wherein the film is between 0.03 and 0.1 mm thick.

19. A method according to claim 11 wherein administering includes percutaneous absorption of the agent.

20. A method for administering a dosage of at least one active agent to a subject, comprising:
  (i) applying to a skin surface of the subject, an amount of a formulation containing water, a first polyvinyl alcohol having a viscosity in the range of from 38 to 55 cPs, a second polyvinyl alcohol having a viscosity in the range of from 13 to 27 cPs and the active agent selected from one or more of a pharmaceutical agent, a wound healing agent and a cosmetic agent but not containing adhesion-promoting polymers other than to polyvinyl alcohol;
  (ii) allowing the formulation to dry on the skin to form a peelable, water-removable agent-releasing film containing the active agent; and
  (iii) administering the dosage of the active agent to the subject from the wet formulation and then from the film.

21. A method according to claim 20, wherein the formulation is administered from a container selected from the group consisting of: an aerosol can, an atomizer, a jar having an apical manual pump, a rollette and a tube container.

22. A method according to claim 21, wherein the formulation is administered in a controlled dosage.

23. A method according to claim 20 wherein the film is at least translucent.

24. A method according to claim 23 wherein the film is transparent.

25. A method according to claim 20 wherein the film is between 0.01 and 0.25 mm thick.

26. A method according to claim 20 wherein the film is between 0.03 and 0.1 mm thick.

27. A method according to claim 20 wherein administering is performed by percutaneous absorption of the active agent.

28. An active agent delivery system comprising:
  a peelable agent-releasing film dried on the skin of a subject so as to be at least translucent, the film administering a dosage of active agent contained in the film into the subject through percutaneous absorption, wherein the film was made from a first polyvinyl alcohol having a viscosity in the range of from 38 to 55 cPs and a second polyvinyl alcohol having a viscosity in the range of from 13 to 27 cPs but not from adhesion-promoting polymers besides polyvinyl alcohol.

29. The active agent delivery system of claim 28 wherein the film has a thickness between 0.01 to 0.25 mm.

30. The active agent delivery system of claim 28 wherein the film has a thickness between 0.03 and 0.1 mm.

31. The active agent delivery system of claim 28 wherein the active agent is a pharmaceutical agent.

32. The active agent delivery system of claim 28 wherein the active agent is a wound healing agent.

33. The active agent delivery system of claim 28 wherein the film is transparent.

34. A method for administering a dosage of at least one active agent to a subject, comprising:
  (i) applying to a skin surface of the subject, an amount of a gel formulation containing water, a first polyvinyl alcohol having a viscosity in the range of from 38 to 55 cPs, a second polyvinyl alcohol having a viscosity in the range of from 13 to 27 cPs and the active agent selected from one or more of a pharmaceutical agent, a wound healing agent and a cosmetic agent;
  (ii) allowing the gel formulation to dry on the skin to form a peelable, water-removable, agent-releasing film capable of overnight adhesion and containing the active agent wherein polymers contributing to said overnight adhesion consist of the first and second polyvinyl alcohols; and (iii) administering by percutaneous absorption, the dosage of the active agent to the subject from the gel and then from the film.

35. A formulation, comprising: an aqueous mixture including a first polyvinyl alcohol having a viscosity in the range of from 38 to 55 cPs, a second polyvinyl alcohol having a viscosity in the range of from 13 to 27 cPs and at least one active agent selected from a pharmaceutical agent, a wound healing agent and a cosmetic agent, the mixture forming a composition, the composition when dried forming an agent releasing, water removable, peelable film capable of overnight adhesion when applied to a skin surface wherein polymers contributing to said overnight adhesion consist of said first and second polyvinyl alcohols.

36. An active agent delivery system comprising:

a peelable agent-releasing film dried on the skin of a subject so as to be capable of overnight adhesion and at least translucent, the film administering a dosage of active agent contained in the film into the subject, wherein the film was made from a first polyvinyl alcohol having a viscosity in the range of from 38 to 55 cPs and a second polyvinyl alcohol having a viscosity in the range of from 13 to 27 cPs wherein polymers contributing to said overnight adhesion consist of said first and second polyvinyl alcohols.

* * * * *